United States Patent
Arnold et al.

(10) Patent No.: US 10,441,513 B2
(45) Date of Patent: *Oct. 15, 2019

(54) ORAL DELIVERY SYSTEM

(71) Applicants: Christian Arnold, Ebersberg (DE);
Armin Armani, Grünwald (DE)

(72) Inventors: Christian Arnold, Ebersberg (DE);
Armin Armani, Grünwald (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/786,938

(22) Filed: Oct. 18, 2017

(65) Prior Publication Data

US 2018/0092813 A1    Apr. 5, 2018

Related U.S. Application Data

(63) Continuation of application No. 14/335,873, filed on Jul. 18, 2014, now Pat. No. 9,820,918.

(30) Foreign Application Priority Data

Apr. 22, 2014 (DE) .................. 20 2014 101 882 U

(51) Int. Cl.

| | |
|---|---|
| A61K 8/02 | (2006.01) |
| A61Q 11/00 | (2006.01) |
| A61K 9/06 | (2006.01) |
| A61K 9/00 | (2006.01) |
| A61K 8/86 | (2006.01) |
| A61K 8/85 | (2006.01) |
| A61K 8/84 | (2006.01) |
| A61K 8/81 | (2006.01) |
| A61K 8/73 | (2006.01) |
| A61K 8/66 | (2006.01) |
| A61K 8/65 | (2006.01) |
| A61K 8/34 | (2006.01) |
| A61K 31/785 | (2006.01) |
| A61K 8/64 | (2006.01) |

(52) U.S. Cl.
CPC .......... *A61K 8/0204* (2013.01); *A61K 8/0216* (2013.01); *A61K 8/345* (2013.01); *A61K 8/64* (2013.01); *A61K 8/65* (2013.01); *A61K 8/66* (2013.01); *A61K 8/731* (2013.01); *A61K 8/732* (2013.01); *A61K 8/817* (2013.01); *A61K 8/8147* (2013.01); *A61K 8/8152* (2013.01); *A61K 8/8158* (2013.01); *A61K 8/8176* (2013.01); *A61K 8/84* (2013.01); *A61K 8/85* (2013.01); *A61K 8/86* (2013.01); *A61K 9/0063* (2013.01); *A61K 9/06* (2013.01); *A61K 31/785* (2013.01); *A61Q 11/00* (2013.01)

(58) Field of Classification Search
CPC ............................. A61K 9/0058; A61Q 11/00
See application file for complete search history.

(56) References Cited

U.S. PATENT DOCUMENTS

| | | | |
|---|---|---|---|
| 4,271,197 A | 6/1981 | Hopkins et al. | |
| 6,200,550 B1 | 3/2001 | Masterson et al. | |
| 6,770,264 B2* | 8/2004 | Stier ....................... | A23G 4/06 |
| | | | 264/148 |
| 2002/0004068 A1 | 1/2002 | Di Drusco | |
| 2004/0115137 A1 | 6/2004 | Verrall et al. | |
| 2007/0140990 A1* | 6/2007 | Fetissova ................. | A61K 8/21 |
| | | | 424/50 |
| 2008/0014224 A1* | 1/2008 | Boyd ................... | A61K 8/0208 |
| | | | 424/401 |
| 2009/0214606 A1 | 8/2009 | Bujard et al. | |
| 2009/0324454 A1 | 12/2009 | Nakano et al. | |
| 2012/0107258 A1 | 5/2012 | Kuhn et al. | |

FOREIGN PATENT DOCUMENTS

| | | |
|---|---|---|
| DE | 102012019194 A1 | 4/2014 |
| EP | 2896396 A1 | 7/2015 |
| WO | WO-2014044869 A3 | 3/2014 |

OTHER PUBLICATIONS

Rohrer, N. et al., "Antimicrobial efficacy of 3 oral antiseptics containing Octenidine, Polyhexamethylene Biguanide, or Citroxx: Can Chlorhexidine be Replaced?" Infection Control & Hospital Epidemiology 31:733-739 (2010).

Rosin, M. et al., "The effect of a polyhexamethylene biguanide mouthrinse compared to an essential oil rinse and a chlorhexidine rinse on bacterial counts and 4-day plaque regrowth," J Clin Periodontol 29(5):392-399 (2002).

Tikus, H.W., "Topical gels containing Chlorhexidine, Vantocil, Fluorophene and animal caries," Helv Odontol Acta 17:105-108 (1973).

Zaugg, L.K., et al., "Antimicrobial activity of short and medium-term application s of polyhexamethylene biguanide, chlorhexidine digluconate and calcium hydroxide in infected immature bovine teeth in vitro," Dent Traumatol 30:326-331 (2013).

* cited by examiner

*Primary Examiner* — Jianfeng Song
(74) *Attorney, Agent, or Firm* — Sterne, Kessler, Goldstein & Fox P.L.L.C.

(57) ABSTRACT

The present invention provides a delivery system for the treatment and/or prevention of infectious pathological changes, including compositions comprising polyhexanide, various pharmaceutical formulations, and processes for using these formulations in oral treatment modalities.

13 Claims, No Drawings

ORAL DELIVERY SYSTEM

CROSS REFERENCE TO RELATED APPLICATION

This application claims priority of German Patent Application, Serial No. 20 2014 101 882.4, filed Apr. 22, 2014, pursuant to 35 U.S.C. § 119(a)-(d), which is incorporated by reference herein in its entirety.

BACKGROUND OF THE INVENTION

Field of the Invention

The present invention relates to an oral delivery system for the treatment and/or prevention of periodontal, peri-implant and other bacterial and viral diseases or fungal diseases in the area of the mouth and throat as well as halitosis: i.e., infectious pathological changes.

Background Information

Infectious pathological changes occur very often and are the main reason for tooth loss/implant loss and halitosis in humans over 35 years of age. An infectious pathological change can be understood to mean an infection or inflammation of the gingival pocket, which, in several steps, can cause loss of the bone holding the tooth/implant. There are different degrees of severity of the condition. Lighter cases relate to the clinically termed gingivitis, whereas more severe cases are clinically called periodontitis/peri-implantitis.

Gingivitis is an inflammation of the gingiva (or of the gums), which is often caused by poor oral hygiene and/or the hormonal state of the patient. It is assumed that the untreated gingivitis develops into a periodontitis/peri-implantitis. Periodontitis is a bacterial disease which attacks the gingival tissue, the teeth, implants and the bone surrounding the teeth implants.

The oral cavity is a substantially aerobe environment through which saliva is flowing. In contrast, the periodontal/peri-implant microenvironment is rather anaerobic and plasma filtrate is flowing through it, which is called "gingival crevicular fluid". The growth of microorganisms within this microenvironment is believed to be responsible for the occurrence of an infectious pathological change. Hence, treatment of said change is directed at monitoring and influencing said growth.

Trials in treating infectious pathological changes by agents which are administered into the oral cavity, such as antibacterial agents, have generally proved ineffective because the periodontal/peri-implant pocket is substantially inaccessible. On the other hand, the systemic administration of antibiotics has only little success in treating periodontal diseases.

Antibacterial agents, such as chlorhexidine and quaternary ammonium salts, in the form of mouth rinses have proved somewhat effective in the prophylaxis/treatment of infectious pathological changes. These agents, however, have different disadvantages. For instance, they are often accompanied by side effects, such as discoloration of the teeth, tongue, mucous membranes or of dental prostheses. Furthermore, these agents oft have a bad taste and affect the patient's sense of taste. Moreover, these agents often disturb wound healing. In addition, the agents are regularly absorbed by the mucous membranes or by the gastro-intestinal tract, which may lead to systemic effects. Further, toxic metabolites are often produced from the abovementioned agents. Another disadvantage lies in that the abovementioned agents usually have to be used at very high concentrations in order to achieve a corresponding effect. Further, allergenic potential was observed. Additionally, the abovementioned agents often have irritant effects and do not have particularly long shelf lives. Moreover, it was observed that blood and proteins influence the effects of these agents.

Pharmaceutical compositions which exhibit a release of agents and which can be introduced into the periodontal cavity and slowly release an antimicrobial agent have been developed. For example, U.S. Pat. Nos. 4,764,377 and 4,892,736 disclose the introduction of tetracycline into non-degradable polymeric fibers which can be wound around the teeth and release the antibiotic in the periodontal cavity over several days. However, the fibers must be fixed in their place with an adhesive and be removed again at the end of the treatment method.

U.S. Pat. No. 4,569,837 discloses the use of water-soluble polymeric substances (e.g., methyl cellulose, gelatin, etc.) as a polymeric matrix for a periodontal implant.

U.S. Pat. No. 5,002,769 discloses a biodegradable system for oral administration with delayed release for treating periodontal diseases. The agent is embedded into a matrix of hydrolyzed gelatin which is cross-linked with glutaraldehyde.

The above-described compositions show varying effectiveness in reducing the bacterial load in the periodontal pocket and in reducing the depth of the pocket. Moreover, these compositions often have the above-mentioned disadvantages.

SUMMARY OF THE INVENTION

It is the object of the present invention to provide an effective delivery system for the treatment and/or prevention of infectious pathological changes which is easy to use and effective at the same time.

The object is attained by an oral delivery system of the kind mentioned above, which comprises polyhexanide.

Polyhexanide has been found to be particularly effective in the use of oral delivery systems for treating and/or preventing periodontal diseases. Polyhexanide can in particular be used in the kind of delivery systems by means of which a slow release in the area of the gingival pockets is to be achieved so that a prolonged contact time is accomplished.

In a preferred version of the oral delivery system, the latter is in a solid pharmaceutical form. A solid pharmaceutical form is particularly advantageous in the use of the system.

In a preferred embodiment of the oral delivery system, the latter is in the form of a chewing gum. Among other advantages, chewing gums counteract the delayed effect observed in polyhexanide because they can be easily used by the patient over a longer period of time, which would be a problem with mouth rinses, for example.

DETAILED DESCRIPTION OF THE INVENTION

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "an aromatic substance" includes one or more aromatic substances, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the an given the context in which it is used, "about" and "approximately" will mean plus or minus <10% of particular term and "substantially" and "significantly" will mean plus or minus >10% of the particular term.

As stated above, in one embodiment of the oral delivery system, the system is in the form of a chewing gum. Chewing gum is generally composed of the following groups of raw materials: gum base or gum mass, plasticizers, filler materials, lubricants, fats, emulsifiers, aromas, dyes, antioxidants, and edible acids for flavoring. As gum mass, either natural materials such as chicle, gutta-percha, latex, benzoin resins or gum arabic or consistency-providing, synthetic thermoplastics, such as polyvinyl acetate in amounts of up to about 65% of the gum mass, polybutadiene styrene, polyisobutylene, isoprene, polyvinyl ether, and polyethylene can be used.

Typical plasticizers are emulsifiers, resins, waxes or glucitol. Typical filler materials are magnesium stearates, chalk, calcium carbonate, silicate or celluloses. The filler materials and technical auxiliary substances maintain flowability and prevent clumping of the particles at low pressure. Mineral oils, microcrystalline waxes or herbal oils are typically used as lubricants, fats or emulsifiers. These auxiliary substances prevent clumping of the formulations and undesired adhesion to instruments in the oral cavity.

Traditional chewing gums can be highly cariogenic because of their high sugar content, but they also massage the gingiva and the salivary glands in case of dry mouth. Chewing gums are also refreshing, vitalizing and/or thirst-quenching owing to the added flavorings.

To avoid the above-mentioned cariogenic effect of sugar in chewing gums, sugar-free chewing gums have been on the market for a long time. Instead of sugar, they contain sugar substitutes, which are mainly sorbitol and xylitol.

The chewing gum according to the invention is intended to support teeth and mouth hygiene and for the treatment/prevention of infectious pathological changes. It is particularly suited for "on-the-go", when there is no opportunity to brush the teeth. The chewing gum according to the invention is usually sugar-free and, similarly to tooth paste, contains traces of minerals for the regeneration of the teeth. The chewing aim according to the invention may also comprise at least one abrasive, in particular calcium carbonate, calcium phosphates, metaphosphates, silicic acid, aluminum oxides, silicates, talcum and/or combinations thereof.

Further, the chewing gum according to the invention may comprise at least one suspending agent or a humectant, in particular water, glycerin, propylene glycol and/or sorbitol syrup, and at least one thickening agent, stabilizer, binder and/or combinations thereof, in particular gels, starches, alginates, oils and/or cellulose gum.

For improving the taste properties, at least one aromatic substance, at least one sweetener and/or at least one sugar substitute, in particular menthol, peppermint oil, sodium saccharin, aspartame, acesulfame, sorbitol, maltitol, xylitol, fructose, and/or combinations thereof, may be added to the chewing gum.

Moreover, the chewing gum according to the invention may comprise further chemical additives, dyes and/or pH regulators, in particular fluorides, astringents, inflammation inhibitors, desensitizers, vitamins, panthenol, white pigments, sodium hydroxide, and/or combinations thereof.

By way of the oral delivery system according to the invention in the form of a chewing gum, the polyhexanide may reach the site of action, in particular the gingival pockets, in a particularly effective manner. The chewing process presses the chewing gum into the gingival pocket, where the polyhexanide is then released.

In another embodiment of the delivery system according to the invention, the latter is in the form of a chip or film, comprising a biodegradable or bioerodible pharmaceutically acceptable polymer.

The chip or film according to the invention is suitable for being implanted into a periodontal pocket and is capable of treating infectious pathological changes in which a delayed release of polyhexanide is desired. The pocket may be a natural pocket, it may be related to a state of disease or it may be intentionally opened as part of the treatment. After implantation, the chip or film softens, swells up and changes into a soft paste, which adheres to the inside of the pocket.

Preferably, the chip or film may comprise at least one cross-linking agent, which is present in an amount sufficient to make the polymer water-insoluble while permitting the release of the polyhexanide from the delivery system.

The film or chip according to the invention preferably comprises a surfactant, which is preferably selected from anionic, cationic, non-ionic surfactants and/or combinations thereof. The non-ionic surfactants can be selected from polyoxyethylene sorbitan fatty acid esters (polysorbate) and sorbitan fatty acid esters.

The chip or film according to the invention is preferably adapted to be administered into a periodontal pocket with in-vivo releasing properties which are aimed at reducing the depth of a periodontal pocket of a patient.

Advantageously, the chip or film according to the invention is in such a form that it is biodegraded within the periodontal pocket, wherein it becomes soil and adheres to the periodontal pocket and wherein, once inserted in a periodontal pocket, it gradually releases the polyhexanide over a period of at least about 24 hours, during which the chip or film converts into a soft material. The chip thus serves as a medium of delivery of polyhexanide as antimicrobial agent for application into the sulcus or gingival pocket. The size of a chip/film according to the invention is generally about 3×3 to about 10×10 mm. In general, the base of the chip/film is a gelatin cross-linked with glutaraldehyde. Cross-linked gelatin has proved particularly suitable for the delayed release of polyhexanide.

Advantageously, the polymer is selected from water-soluble protein, cellulose or a cellulose derivative, starch or a starch derivative, glyceryl monostearate, carbomer, PVP (polyvinyl pyrrolidone), gum, acacia gum, guar gum, polyvinyl alcohol, polyhydroxyethyl methacrylate, polyhydroxymethyl methacrylate acrylic acid, polyacrylamide, polyethyleneglycolene, polyacetic acid, polyglycolic acid, copolymers of polyacetic acid and polyglycolic acid, polyanhydrides and polyorthoesters. The water-soluble protein is preferably selected from the group consisting of gelatin, collagen, albumin, an enzyme and fibrinogen.

In another embodiment of the system according to the invention, the latter is in the form of a gel or salve. In this form, it is usually introduced into the gingival pockets, where it releases polyhexanide to the surroundings.

The gel or salve according to the invention is for intraoral application, in particular for application into the sulcus or into a gingival pocket. The polyhexanide here again serves as an antimicrobial agent. The gel/salve according to the invention may be based on a conventional ethanol/glycerol/macrogol compound.

The gel according to the invention or the salve according to the invention may be both a ready-to-use preparation and a mixing system. In case of a mixing system, certain components are mixed only shortly prior to the application and brought to the diseased site. This has the advantage, among others, that a mixing system is easy to process after mixing. For instance, in one embodiment, a viscous mass may at first be present after mixing which hardens only after it has been introduced into the mouth. This significantly simplifies the application. The mixing system may be in the form of a mixing capsule, for example.

As compared to the known antibacterial agents, such as chlorhexidine, the oral delivery system according to the invention has decisive advantages. For instance, the polyhexanide used in the oral delivery system according to the invention is not cytotoxic. Additionally, no side effects, such as discoloration of the teeth, tongue, mucous membranes or of dental prostheses can be observed. The used polyhexanide is tasteless and does not compromise the sense of taste. Further, it does not disturb wound healing and reduces fibrin formation. Furthermore, it is not known to be absorbed by the mucous membranes or via the gastro-intestinal tract. Further, no toxic metabolites form during use. Another significant advantage lies in the fact that the effective concentration of polyhexanide is many times lower than that of chlorhexidine. Further, polyhexanide has no allergenic potential and no irritant effect. As far as is known, polyhexanide is not sensitizing. The shelf life of polyhexanide is also longer than in conventional agents. Moreover, no development of resistance has been observed. Polyhexanide has a broad effective spectrum and shows very little protein and blood interference (effect is hardly influenced by proteins or blood).

Although the invention has been described with reference to the above disclosures, it will be understood that modifications and variations are encompassed within the spirit and scope of the invention. Accordingly, the invention is limited only by the following claims.

All references recited in this disclosure are incorporated by reference herein in their entireties.

We claim herein:

1. A chewing gum comprising an antibacterial agent in an amount effective to treat infectious pathological changes in the mouth and throat, wherein the antibacterial agent is the only antibacterial agent in the chewing gum and wherein the antibacterial agent consists of polyhexanide and optional fluoride.

2. The gum of claim 1, wherein the gum further comprises at least one suspending agent or humectant selected from the group consisting of water, glycerin, propylene glycol, sorbitol syrup, and combinations thereof.

3. The gum of claim 1, wherein the gum further comprises at least one thickening agent, stabilizer, or binder.

4. The gum of claim 3, wherein the at least one thickening agent, stabilizer, or binder is selected from the group consisting of a gel, a starch, an alginate, an oil, a cellulose gum, and combinations thereof.

5. The gum of claim 1, wherein the gum further comprises a gum base selected from the group consisting of chicle, gutta-percha, latex, benzoin resin, and gum arabic.

6. The gum of claim 1, wherein the gum comprises a synthetic thermoplastic gum base.

7. The gum of claim 6, wherein the synthetic thermoplastic is selected from the group consisting of polyvinyl acetate, polybutadiene styrene, polyisobutylene, isoprene, polyvinyl ether, and polyethylene.

8. The gum of claim 1, wherein the gum comprises a filler selected from the group consisting of magnesium stearate, chalk, calcium carbonate, a silicate, and a cellulose.

9. The gum of claim 1, wherein the gum comprises at least one aromatic substance, sweetener, or sugar substitute.

10. The gum of claim 9, wherein the at least one aromatic substance, sweetener, or sugar substitute is selected from the group consisting of menthol, peppermint oil, sodium saccharin, aspartame, acesulfame, sorbitol, maltitol, xylitol, fructose, and combinations thereof.

11. The gum of claim 1, wherein the gum comprises an emulsifier, a resin, a wax, or glucitol.

12. The gum of claim 1, wherein the gum comprises an abrasive selected from the group consisting of calcium carbonate, calcium phosphate, a metaphosphate, silicic acid, an aluminum oxide, a silicate, talcum, and combinations thereof.

13. The gum of claim 1, wherein fluoride is present in the antibacterial agent.

* * * * *